(12) United States Patent
Reyes

(10) Patent No.: US 9,956,062 B2
(45) Date of Patent: May 1, 2018

(54) ORAL CAVITY SUCTION DEVICE

(71) Applicant: Hari Mark Reyes, Portland, OR (US)

(72) Inventor: Hari Mark Reyes, Portland, OR (US)

(*) Notice: Subject to any disclaimer, the term of this patent is extended or adjusted under 35 U.S.C. 154(b) by 0 days. days.

(21) Appl. No.: 15/146,567

(22) Filed: May 4, 2016

(65) Prior Publication Data

US 2017/0156831 A1 Jun. 8, 2017

Related U.S. Application Data

(60) Provisional application No. 62/263,867, filed on Dec. 7, 2015.

(51) Int. Cl.
*A61C 5/14* (2006.01)
*A61C 17/06* (2006.01)

(52) U.S. Cl.
CPC .............. *A61C 17/043* (2013.01); *A61C 5/14* (2013.01)

(58) Field of Classification Search
CPC ..... A61C 17/043; A61C 17/0208; A61C 5/14; A61C 17/04

USPC ..... 433/91–96; 600/156, 237, 239, 242, 387
See application file for complete search history.

(56) References Cited

U.S. PATENT DOCUMENTS

| 4,017,975 | A | * | 4/1977 | Johnson | ............... | A61C 17/043 |
| | | | | | | 433/91 |
| 6,474,990 | B1 | * | 11/2002 | Hoffman | ............... | A61C 17/043 |
| | | | | | | 433/126 |
| 9,044,293 | B2 | * | 6/2015 | Reyes | ................. | A61C 17/043 |

\* cited by examiner

*Primary Examiner* — Ralph Lewis
(74) *Attorney, Agent, or Firm* — Mark S Hubert

(57) ABSTRACT

A disposable saliva ejector with a single planar, double leaf shaped plate design embossed on the inner faces of the leaf plates with a series of arced ribs and then folded about its midpoint. A tab and slot arrangement joins the two plates when operationally folded. The arced ribs form a series of channels equidistant about the perimeter of the device. A trough runs along the linear axis of both of the plates to direct any fluid and debris that is sucked into the channels into a connected suction tube. Placement of the saliva ejector within the mouth lies along the interior of the patient's cheek, keeping the oral cavity clear of viewing obstructions.

15 Claims, 3 Drawing Sheets

ORAL CAVITY SUCTION DEVICE

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to an oral cavity suction device, and more particularly to a dental saliva ejection device.

BACKGROUND

Oral cavity suction devices, also known as saliva ejectors are narrow vacuum tubes that dental health professionals employ for removing saliva, water, and debris during a dental procedure. Often saliva ejectors will "sit" in a patient's mouth during a dental procedure in order to continuously rid the mouth of excess saliva, water, and debris to facilitate uninterrupted work by the dental health professional. The ejector tubes are typically made of a pliable plastic with a metal wire embedded within its wall to allow the tube to be bent to a desired angle and maintain that angle. If the tip of the suction tube contacts the patient's mouth tissue, it can suck the tissue into contact with the tip of the ejector, thereby rendering the ejector useless, since it is no longer removing excess saliva, water, and debris, not to mention causing a very uncomfortable sensation for the patient. Due to this fact the dentist preforming the work on the patient must be assisted at all times.

A disposable, cost effective, comfortable, and efficient saliva ejector that can be managed in a patient's mouth without the need for a dental assistant, would be a welcome addition to the dental industry. Such a device is provided by the embodiments set forth below.

BRIEF SUMMARY

In accordance with various embodiments, an improved saliva ejector is provided.

The saliva ejector of the present invention solves the aforementioned problems by employing a tapered, ovate shape. The saliva ejector of the present invention resides along the left or right-side buccal mucosa allowing for full view of the oral cavity. When the device is positioned along the buccal mucosa, it alleviates the patient's natural gag reflex, and is out of the way of most dental procedures. Since it has a plethora of arced passaged formed about the perimeter of the device when assembled, and is non collapsible, it provides a continual strong suction field where it is needed, yet does not tug on the patient's buccal mucosa and inner cheek. The ejector's slender profile aids in positioning the saliva ejector within the patient's mouth, resulting in a more effective, gentler and comfortable saliva ejector. When coupled to a suction tube with a "U" bend, the combination may be placed adjacent the outside of the patient's cheek with the remaining tubing running back below the patient's ear such that the entire oral cavity suction system (the saliva ejector, the vacuum and the suction tube) is out of the dentist's way and requires little if any attention.

The patient can easily adjust his bite without the removal of the suction system, as well as relieve the water/saliva from his mouth by simply closing his mouth, thereby allowing the dentist or hygienist to work without an assistant constantly providing suction.

The saliva ejector of the present invention also maximizes the patient's comfort if he has lingual gum sensitivity, temporomandibular joint (TMJ) issues, or mandibular or maxillary tori; these regions are simply not contacted due to the devices's unique geometry, and its placement within the mouth.

The saliva ejector of the present invention allows simplified fabrication and assembly of the device. It allows a planar fabrication and assembly about the axial centerline of the device. The processes utilized in fabrication are simplified and the number of fabrication steps are reduced.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION OF CERTAIN EMBODIMENTS

Figure 1:
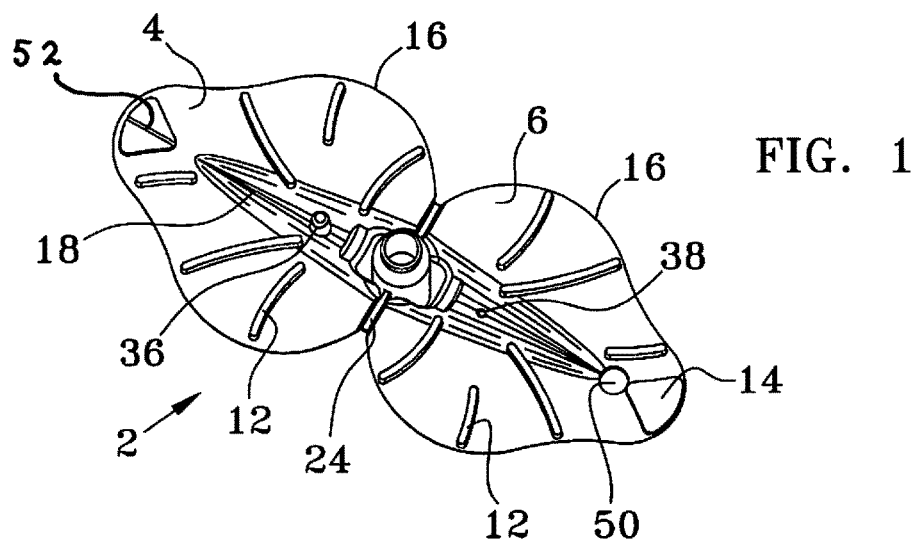
FIG. 1 is a top perspective view of the unassembled saliva ejector.

Looking at FIG. 1 it can be seen that the saliva ejector 2 is a pair of substantially similar leaf shaped (ovate) plates with their proximal ends hingedly connected together into a mirror image configuration with a short tube extending normally above and below the plates from a cutout region at the center of the ejector's axial centerline, where the two plates are conjoined. However, upon closer examination it can be seen that this device is much more structurally complex as will be discussed herein.

Figure 8:
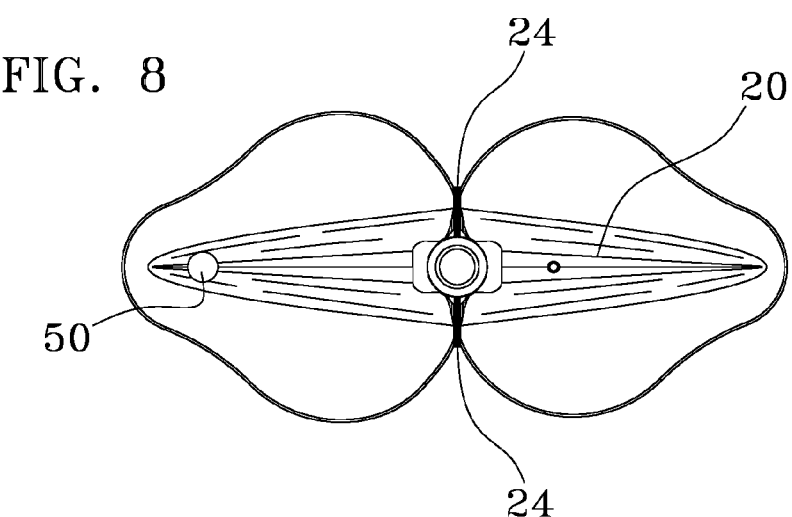
FIG. 8 is a bottom view of the unassembled saliva ejector.
Figure 9:
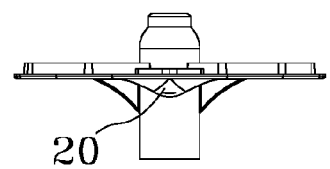
FIG. 9 is a second end view of the unassembled saliva ejector.

There is a unique geometry to the saliva ejector 2, which can generally be described as ovate (i.e., having a wider base than apex and referred to herein also as a leaf shape), such that each plate has two distinct regions, its body 1, and its front lobe 3 (FIG. 8). Combined, these regions are referred to as leaf shaped plates. Each plate is a flexible, generally planar member that is constructed from a medical grade polymer of uniform thickness.

The saliva ejector 2 is made of a first leaf shaped inner plate 4 and a slightly larger, second leaf shaped cheek plate 6. (As denoted, in use, the inner plate 4 faces the patient's mouth's midline and the cheek plate 6 faces the patient's cheek.) The peripheral edges 16 of these two plates trace an identical outline however, these two plates are not identically dimensioned. (In the alternate embodiment, the two plates are identically dimensioned.) In the preferred embodiment, the second, cheek plate 6 is dimensioned so as to be approximately 2 mm larger measured along any line drawn across the device 2. Simply stated, the perimeter edge of the second cheek plate 6 extends approximately 1 mm beyond the perimeter edge of the first inner plate 4.

The plates each are adorned on their interior faces 8 and 10 (FIG. 4) with a series of raised, arced ribs 12 that extend normally therefrom. (As used herein, the term rib refers to any raised projection or embossing extending from the inner faces of the plates.) At the distal ends of each plate there is a raised pad 14. The raised pad 14 on the second cheek plate 6 has a slot 52 cut along its full length but only partially through its depth.

Each of the ribs 12 are the same height and width. The raised pads 14 extend only one half of the height from the interior face of the plates that the ribs 12 do. The raised pads serve to define the depth and width of the first channel and keep the tip 76 from collapsing upon itself when suction is applied to the device. The slot 52 allows for pooled saliva to be drawn from the foremost tip of the device 2 when inserted into a patient's mouth.

Figure 2:
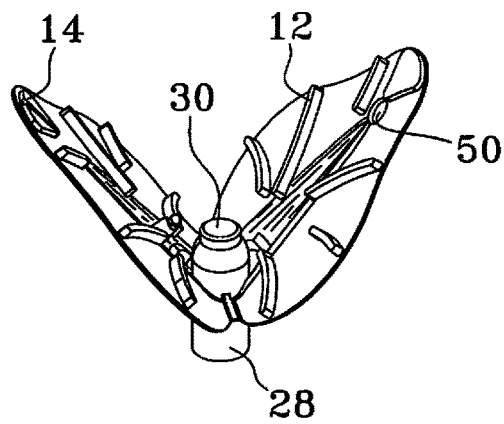
FIG. 2 is a front perspective view of the saliva ejector being assembled.
Figure 3:
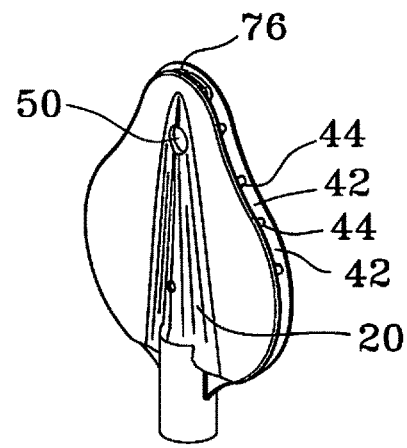
FIG. 3 is a front perspective view of the assembled saliva ejector.

Along the linear centerline of each plate is formed an identical trough 18. The troughs 18 are open tapered grooves on the interior faces (FIGS. 1, 2 and 4) that have a raised ridge 20 on the exterior faces 32 and 34 (FIGS. 3, 5, 6, 7, 8 and 9). The taper in the grooves begin at the proximal ends of the plates and extend along the linear centerline but terminate before the raised pads 14 at the distil ends of each plate. The troughs taper in both width and depth, diminishing in these dimensions from the proximal end toward the distal ends. The proximal ends of each plate have a cutout 22 centered about the linear centerline of the plate.

The proximal ends of the two leaf shaped plates are hingedly conjoined together on a pair of triangular gusset supports 24 (FIGS. 5, 6, 7, 8 and 9) that extend from opposite sides of the circular connection tube 26, 180 degrees apart. The gusset supports 24 extend perpendicularly from the axial centerline of the void formed by the joined cutouts 22. Stated otherwise, the gusset supports 24 are formed along the distal end of each of the plates. This is also the axial centerline of the unassembled device. The plane of each of the gusset supports 24 resides perpendicular to the plane of the plates when in the unassembled saliva ejector 2. When the device is assembled, their planes lie parallel but not collinear with each other and the linear axes of the two plates lie parallel in all three planes. The thickness of the gusset supports 24 approximates the height of the ribs. The plates are attached to opposite sides of the gusset supports 24.

There is a suction orifice 50 formed through the first inner plate 4 (adjacent to the raised pad 14 at the distal end of the plate as is illustrated in FIGS. 1, 2, 3 and 8. This suction orifice 50 coincides with the end of the trough 18 formed on that plate. When the saliva ejector 2 is connected to a suction device and placed properly along the buccal mucosa within the patient's mouth, the inner face of the first plate 4 of the saliva ejector 2 will face toward the midline of the patient's mouth. In this way there will always be suction at the proximal end of the device, either through the suction orifice 50 or the slot 52 in the pad 14 on the second, cheek plate. This is important, as the tip of the distal end of the device is the point where saliva pools in the patient's mouth.

A vacuum connection end 28 extends from the exterior end of the circular connection tube 26 and a tapered saliva inlet end 30 extends from its interior end when the device 2 is assembled. The vacuum connection end 28 is dimensioned for frictional connection to a suction tube which is operationally connected to a vacuum system. In combination with the saliva ejector 2, these elements form a saliva ejection system.

Centered in the open tapered groove of the trough 18 on the first plate 4 is a circular tab 36 that is matingly conformed for frictional retention in a circular slot 38 that is formed in the open tapered groove 18 on the second plate 6. These are engaged for assembly of the device 2.

When the saliva ejector 2 is assembled (FIG. 2) the cheek plate 6 overlaps the inner plate 4 about its peripheral edges. The saliva inlet end 30 of the connection tube 26 lies inside partially within the cutouts 22 and partially within the tapered groove between the inner faces of the first and second plates. The vacuum connection end 28 extends from the linear centerline of the proximal end of the device. The saliva end matingly conforms for a frictional fit within the open tapered groove. Since the connection tube and the two plates are all made of a flexible polymer, when a suction is applied to the device, these components are drawn together within closer tolerances.

The ribs 12 are arced from the peripheral edge of their respective plates toward the open tapered trough 18 on the interior faces of the plates. The arced ribs 12 do not lie in the same pattern on the two different plates. Rather, the ribs of the two plates lie in symbiotic patterns such that, when the device is assembled and the two plates are folded inward, about the gusset supports 24 (with their inner faces toward each other) so as to reside in a spaced parallel orientation (FIG. 3), a series of adjacent, arced channels 42 are formed leading from the peripheral edge 16 of the device to the trough 18. These arced channels 42 are approximately equally spaced about the peripheral edge 40 of the assembled saliva ejector 2, (as are the rib ends 44). Thus, the two plates 4 and 6 in the body of the saliva ejector 2 are supported from collapse (their interior faces being drawn into contact with each other by the vacuum) by the height of the ribs. The distil ends of the saliva ejector 2 are prevented from collapse by the raised pads 14. This ensures that the device will always be able to draw saliva and debris from the channels into the trough 18 and out the connection tube 26.

Figure 4:
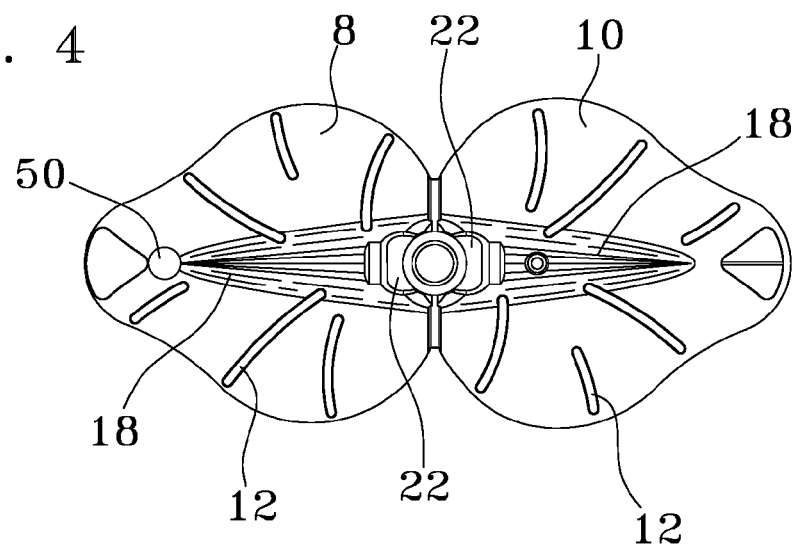
FIG. 4 is a top view of the unassembled saliva ejector.
Figure 5:
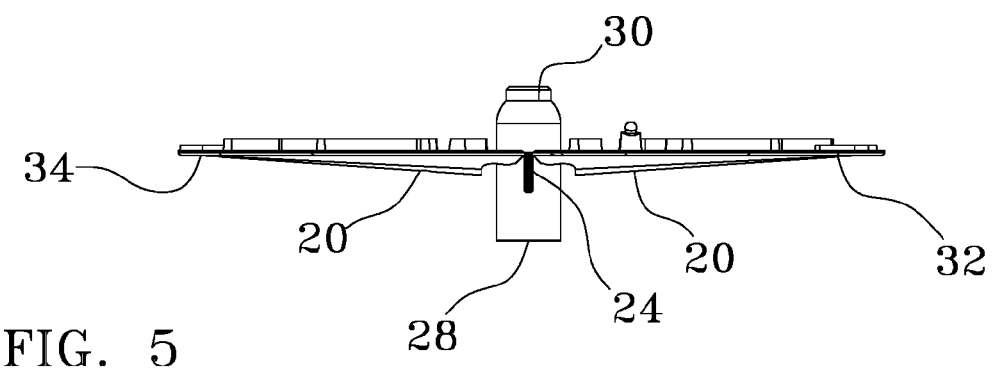
FIG. 5 is a right side view of the unassembled saliva ejector.
Figure 6:
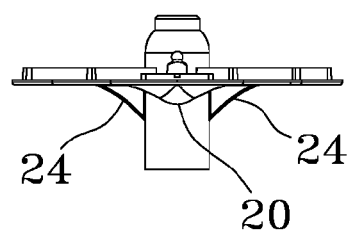
FIG. 6 a first end view of the unassembled saliva ejector.
Figure 7:
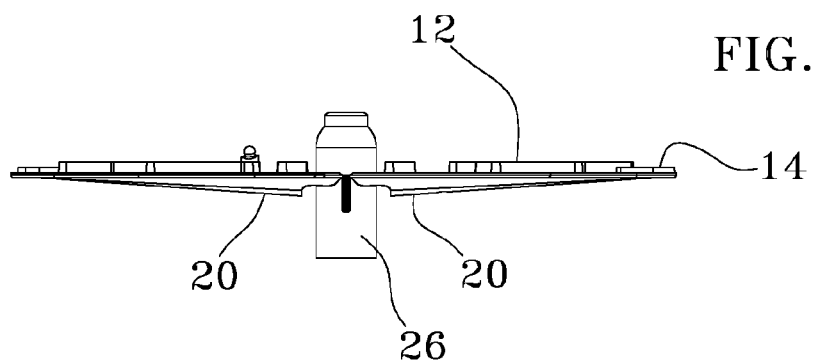
FIG. 7 is a left side view of the unassembled saliva ejector.

As can be seen with reference to FIGS. 4 to 6, the arced ribs 12 and the arced channels 42 lie on the same plane as the open tapered trough 18 and through which the linear axis of the device 2 lies. When the two plates are assembled, (FIG. 3) the series of adjacent, arced channels that span between the trough and the peripheral edge of the device, exit the device 2 at the peripheral edge 40, between the first plate 4 and the second plate 6, along a path which is parallel to the outer planar faces of the assembled device 2. As such, saliva and debris are drawn into the device in arced streams that reside in the same plane as the linear axis of the device. And parallel to the faces of the plates.

One of the remarkable features of the physical structure of the saliva ejector 2 is that lends itself to simple, economical production. The entire device is made by injection molding of a flexible dental grade polymer. Since it lays flat prior to assembly the saliva ejector 2 can be stacked for mass shipping.

The device 2 is designed to lie between the buccal regions of the oral cavity and the inner cheek, so as to not rely on teeth for support. The U shaped discharge section of the suction tube curves around the oral commissure and then along the outside of the cheek. The placement of the saliva ejector 2 is key to its function, since saliva pools in the lower regions of the oral cavity toward the throat. When properly placed within a patient's mount, saliva ejector effectively removes the pooled saliva while not impeding the dentist's work. Once placed, saliva ejector is comfortable for the patient and does not need constant monitoring from a dental assistant. The different outer dimensions of the two plates prevent the patient's cheek from being suctioning into contact with the channels. The suction tube is connected to a suction device and once the suction device is turned on a diffuse yet effective suction field is created.

No matter how the teeth are aligned or shaped, or even if the patient has missing teeth, the saliva ejector 2 will be fully supported and still function properly.

When the saliva ejector 2 connected to a saliva ejection system, and is inserted into the patient's mouth alongside their inner cheek, when the vacuum is initiated, the saliva and debris from the patient's mouth is sucked in from the peripheral edge 16 of the device 2 through the arced channels 42, into the trough 18, through the connection tube 26 and into the remainder of the saliva ejection system. Since the larger of the two plates, the inner cheek plate 6 lies against the patent's check, there is a stepdown in the periphery edges of the plates and the vacuum created will not draw the patient's cheeks into contact with the peripheral edge of the saliva ejector and across the channels so as to block the flow of saliva.

Although not illustrated herein, the suction tube that the vacuum connection end of the of the connection tube 26 connects to is hollow, has a proximate end, a distal end, and is generally "U" shaped. The suction tube can be reusable or disposable. It is through this tube that saliva ejector 2 is connected to a suction device (well known in the field of dentistry and not shown), and through which saliva, water, and other debris are removed from the mouth of a patient.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

I claim:

1. A saliva ejector comprising:
   a pair of generally ovate shaped plates, having a linear axis, distal ends, proximal ends, an inner face and an outer face, and perimeter edges;
   a suction connection tube disposed between said plates and residing adjacent to said proximal ends, said connection tube having a vacuum connection end and a saliva inlet end;
   an open trough formed thereon said inner faces residing along said linear axes;
   a series of channels formed on said plates, said channels leading from said perimeter edge of the device to the trough, said channels exiting between said plates;
   wherein said planar plates are hingedly attached at said proximal ends so as to allow a folding between an assembled and unassembled saliva ejector.

2. The saliva ejector of claim 1 wherein said trough formed thereon said inner faces is sized for frictional engagement with said saliva inlet end of said suction connection tube in said assembled saliva ejector.

3. The saliva ejector of claim 2 further comprising a series of embossings formed thereon said inner faces wherein said embossings include a series of ribs, said ribs extending a first height above said inner faces of said plates.

4. The saliva ejector of claim 3 wherein said ribs extend between said open trough and said perimeter edges.

5. The saliva ejector of claim 4 wherein said series of open channels are formed between adjacent said ribs in said assembled saliva ejector.

6. The saliva ejector of claim 5 wherein said open channels are equally spaced about said perimeter edge of said saliva ejector.

7. The saliva ejector of claim 6 further comprising:
   a tab formed thereon said first plate; and
   a matingly engageable slot formed therein said second plate;
   wherein said tab and said slot may be frictionally engaged to assemble said saliva ejector.

8. The saliva ejector of claim 3 wherein said embossings further comprise a pad extending from said distil end of each said plate, said pads having a second height above said inner faces of said plates.

9. The saliva ejector of claim 8 wherein said second height is approximately one-half of said first height.

10. The saliva ejector of claim 2 wherein said open trough has both a depth and a width on said inner faces and a raised ridge on said outer faces, and wherein said trough tapers in both said width and said depth, diminishing in these dimensions from the proximal ends toward the distal ends of the plates.

11. The saliva ejector of claim 1 wherein assembled, said saliva ejector plates are held in a spaced parallel configuration with said embossings there between.

12. The saliva ejector of claim 1 further comprising a pair of gussets affixed normally to said suction connection tube and residing between said distal ends of said plates, and wherein said distal ends of said plates are hingedly affixed to said gussets.

13. A saliva ejector comprising:
   a first leaf shaped inner plate and a second leaf shaped cheek plate, each having distal ends, proximal ends, an inner face and an outer face, and identically shaped perimeter edges;
   a suction connection tube with a pair of gusset plates extending normally from opposite sides of said connection tube, said connection tube having a vacuum connection end and a saliva inlet end, wherein said proximal ends of said first leaf shaped plate is hingedly affixed to a first side of said gusset plates and said second leaf shaped plate is hingedly affixed to a second side of said gusset plates;
   a pattern of raised ribs formed thereon said inner faces, wherein said pattern of ribs on said first leaf and said pattern of embossings on said second leaf are not identical patterns;
   a groove formed along a linear centerline of said plates, said groove dimensioned to accept said saliva inlet end of said connection tube;
   wherein said saliva ejector may be assembled by folding said first plate and said second plate about said gusset plates to place said plates into a parallel, spaced configuration wherein a series of open channels are formed between adjacent ribs and between first leaf shaped inner plate and a second leaf shaped cheek plate, said channels exiting said saliva ejector between said plates along said perimeter edge.

14. The saliva ejector of claim 13 wherein said a first leaf shaped inner plate is smaller than said second leaf shaped cheek plate.

15. The saliva ejector of claim 14 wherein said second leaf shaped cheek plate perimeter edge extends beyond said perimeter edge of said first leaf shaped interior plate when saliva ejector is assembled.

\* \* \* \* \*